(12) United States Patent
Kloeffel et al.

(10) Patent No.: US 10,792,412 B2
(45) Date of Patent: Oct. 6, 2020

(54) METHOD FOR VENTING A DIALYZER

(71) Applicant: FRESENIUS MEDICAL CARE DEUTSCHLAND GMBH, Bad Homburg (DE)

(72) Inventors: Peter Kloeffel, Nuedlingen (DE); Thomas Nuernberger, Burkardroth (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 287 days.

(21) Appl. No.: 15/748,392

(22) PCT Filed: Jul. 27, 2016

(86) PCT No.: PCT/EP2016/001301
§ 371 (c)(1),
(2) Date: Jan. 29, 2018

(87) PCT Pub. No.: WO2017/016662
PCT Pub. Date: Feb. 2, 2017

(65) Prior Publication Data
US 2018/0214627 A1  Aug. 2, 2018

(30) Foreign Application Priority Data
Jul. 29, 2015 (DE) .......... 10 2015 009 886

(51) Int. Cl.
*A61M 1/36* (2006.01)
(52) U.S. Cl.
CPC .......... *A61M 1/3627* (2013.01); *A61M 1/365* (2014.02); *A61M 1/3643* (2013.01); *A61M 1/3644* (2014.02); *A61M 1/3649* (2014.02); *A61M 1/3652* (2014.02); *A61M 2205/18* (2013.01); *A61M 2205/3331* (2013.01); *A61M 2205/705* (2013.01)

(58) Field of Classification Search
CPC .. A61M 1/3627; A61M 1/3629; A61M 1/363; A61M 1/3643; A61M 1/3644; A61M 1/3649; A61M 1/365; A61M 1/3652; A61M 2205/18; A61M 2205/3331; A61M 2205/705
See application file for complete search history.

(56) References Cited

U.S. PATENT DOCUMENTS

2004/0084371 A1* 5/2004 Kellam ................. A61M 1/288
210/646
2013/0150768 A1 6/2013 Sakamoto et al.

FOREIGN PATENT DOCUMENTS

DE     102011102492     11/2012
WO     WO 2004/043520   5/2004

* cited by examiner

*Primary Examiner* — Philip R Wiest
(74) *Attorney, Agent, or Firm* — Jacobson Holman, PLLC.

(57) ABSTRACT

A method for venting a dialyzer which has a dialyzate chamber, a blood chamber and a semi-permeable dialyzer membrane separating these two chambers. An overpressure is generated in the dialyzate chamber with respect to the blood chamber for removing air inclusions lying at the surface of the membrane at the dialyzate chamber side after a filling of the dialyzate chamber and before a filling of the blood chamber.

18 Claims, 2 Drawing Sheets

METHOD FOR VENTING A DIALYZER

BACKGROUND OF THE INVENTION

1. Field of the Invention

The invention relates to a method for venting a dialyzer and in particular for removing air inclusions lying at the surface of the membrane at the dialyzate chamber side after filling the dialyzate chamber within the framework of priming. The invention further relates to a dialysis machine having a control unit on which an algorithm for carrying out such a method is stored.

2. Description of the Related Art

Air inclusions lying at the dialyzer membrane have the result that no mass transfer (diffusion) can take place at the corresponding points during the dialysis. Membrane surface is thus lost for the treatment and the efficiency (clearance) of the treatment is reduced.

A priming of the dialyzer takes place before carrying out the dialysis process, wherein the dialyzate chamber and the blood chamber of the dialyzer are filled with a priming fluid. The problem of air inclusions which lie at the dialyzer membrane in particular often occurs when filling the dialyzate chamber of capillary dialyzers. These air inclusions can only be removed by an intervention of the user after the filling.

It is known for the avoidance or removal of such air inclusions to fill the dialyzate chamber from the bottom to the top and optionally additionally to knock the dialyzer. The dialyzer subsequently has to be rotated to fill the blood chamber.

A further known method provides a filling of the dialyzate chamber from top to bottom, which has the advantage that the dialyzer does not have to be rotated by the user for filling the blood chamber. A comparatively low filling speed is, however, important for a good result here and a small quantity of air also remains in the dialyzate chamber in this case.

SUMMARY OF THE INVENTION

It is the object of the invention to provide an improved method for venting a dialyzer.

This object is achieved in accordance with the present invention by a method for venting a dialyzer which has a dialyzate chamber, a blood chamber and a semipermeable dialyzer membrane separating these two chambers. Within the framework of the method—after a filling of the dialyzate chamber and before a filling of the blood chamber—an overpressure is generated in the dialyzate chamber with respect to the blood chamber for the removal of air inclusions lying at the surface of the membrane at the dialyzate chamber side.

The overpressure in the dialyzate chamber with respect to the blood chamber can also be generated in that a vacuum is generated in the blood chamber. It can also be generated, for example, in that the blood chamber is vented and an overpressure is generated in the dialyzate chamber relative to the atmospheric pressure.

"Overpressure in the dialyzate chamber" is to be understood such that the pressure in the dialyzate chamber is above that in the blood chamber.

The filling of the dialyzate chamber and/or of the blood chamber typically takes place using a priming fluid, for example using a dialysis fluid or a saline solution.

Since the blood chamber has not yet been filled at the time of the generation of the overpressure, it is still gas-filled and typically air-filled. The surface of the membrane at the blood chamber side is therefore not wetted. As long as the typically hydrophobic membrane is not wetted at both sides, it has a high barrier effect for a water-based priming fluid. An overpressure can therefore be built up in the dialyzate chamber.

If now regions of the surface at the dialyzate chamber side are also not wetted due to undesired air inclusions, the membrane is still dry regionally—namely below the air inclusions—before the generation of the overpressure. The typically hydrophobic membrane has a high gas permeability and in particular air permeability in such a dry state.

Air inclusions lying at the surface of the membrane at the dialyzate chamber side can therefore be pressed through the membrane into the still not filled blood chamber and can be led off with a prevailing overpressure.

The dialyzer membrane is therefore in summary permeable for air—as long as it is still dry, as is the case with air inclusions. Overpressure in the dialyzate chamber ensures that the residual air is pressed through the membrane into the still empty blood chamber. A saving in time with an improved venting can be achieved by a faster filling and by the subsequent carrying out of the method in accordance with the invention (pressure-controlled filling method) with respect to some known flow-controlled filling processes which are directed to keep air inclusions in the dialyzate chamber as low as possible.

The semipermeable dialyzer membrane is preferably a membrane which has hydrophobic properties at least in the dry state.

In an embodiment, the overpressure is in a range up to 2 bar. An overpressure is preferably between 50 and 500 mmHg. Preferred ranges comprise the range between 140 and 220 mmHg and in particular the range between 175 and 195 mmHg. These overpressures are sufficient for pressing the air inclusions through the membrane and are simultaneously small enough not to cause any damage to the filter.

In an embodiment, the blood chamber is vented toward the environment during the generation of the overpressure. If the blood chamber is vented toward the atmosphere, the residual air passing over can escape and thus no counter-pressure can build up.

In an embodiment, the dialyzate chamber is connected to a fluid-conducting system at the infeed and/or return side during the carrying out of the method. Provision is preferably made that the dialyzate chamber is integrated into the dialyzate circuit of a dialysis machine.

Provision can be made that the blood chamber is also already integrated into the blood circuit of a dialysis machine during the carrying out of the method.

The method is preferably carried out during the priming procedure of the fluid-conducting lines in a dialysis machine. The method is preferably carried out automatically or after a user input using a control unit of the dialysis machine.

In an embodiment, the overpressure is generated by the closing of a valve arranged at the return side of the dialyzate chamber and by the simultaneous conveying of further fluid into the dialyzate chamber from the feed side of the fluid-conducting system.

The conveying of further fluid from the feed side of the fluid-conducting system into the dialyzate chamber can take place by a pump and/or by a balancing system such as a balance chamber which is anyway present in the dialysis machine. A supply pump arranged in the feed line can in particular be used. Provided that a closed circuit is formed during the priming or flushing, the use of an ultrafiltration pump or of a return pump located in the return line of the dialyzer is also conceivable provided that they are suitable for this purpose.

In an embodiment, any desired valve arranged in the dialyzate circuit at the return side of the dialyzer can serve as a return valve. A valve can be used which is anyway present in the return line or a valve which is specifically provided for carrying out the method in accordance with the invention.

A pressure measurement in the dialyzate chamber can take place, for example, by a pressure sensor arranged between the pump and the dialyzate chamber, between the dialyzate chamber and the valve or at the dialyzer itself.

In an embodiment, the pressure build-up is stopped after reaching a predefined overpressure value in the dialyzate chamber. This can be achieved, for example, by stopping the pump. The predefined overpressure value can be in the previously described ranges.

In an embodiment, the overpressure in the dialyzate chamber is maintained over a venting period after the stopping of the pressure build-up. This can be achieved, for example, by keeping the valve closed. The maintenance of the overpressure does not mean that the pressure remains constant in the dialyzate chamber over the venting time period. Pressure drops rather result on the escaping of air inclusions lying at the membrane or due to other influences.

In an embodiment, the pressure prevailing in the dialyzate chamber and/or its development is/are measured during the pressure build-up. Alternatively or additionally, the pressure prevailing in the dialyzate chamber and/or its development can be measured in the course of the venting time period.

In an embodiment, a characteristic of the measured pressure development in the in the venting time period is used to selectively initiate a repeat of the process or a continuation of the priming procedure. The continuation of the priming procedure is to be understood, for example, as a flushing procedure of the dialyzate chamber taking place subsequent to the method in accordance with the invention or a filling of the blood chamber taking place subsequent to the method in accordance with the invention.

Provision can furthermore be made that the characteristic is used to output a signal which is representative for the venting state of the dialyzate chamber.

The characteristic can be the increase in the pressure/time curve, the duration up to a partial or complete depletion of the overpressure or the like.

The indicated steps can be carried out automatically by the control unit of the dialysis machine.

Alternatively or additionally, for example, it can also be determined gravimetrically whether air inclusions are still present in the dialyzate chamber or not.

In an embodiment, a characteristic related to the measured pressure development during the pressure build-up is compared with a corresponding stability criterion which is representative for the integrity of the dialyzer membrane and/or the integrity of interfaces of the dialyzate chamber with the fluid-conducting system. A warning signal it emitted by the machine on a deviation of the characteristic from the stability criterion.

The characteristic can, for example, be the maximum fluid supply which is required for building up a specific pressure in the dialyzate chamber.

The method in accordance with the invention is anyway carried out before the start of a dialysis treatment when the patient is not yet connected to the machine.

The invention furthermore relates to a dialysis machine having a dialyzate circuit and a dialyzer which has a dialyzate chamber integrated into the dialyzate circuit, a blood chamber and a semipermeable dialyzer membrane separating these two chambers. The dialysis machine is characterized in accordance with the invention in that it has a control unit which is configured to carry out a method in accordance with the invention.

BRIEF DESCRIPTION OF THE DRAWINGS

Further details and advantages of the invention result from the following embodiment described with reference to the Figures. There are shown in the Figures.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
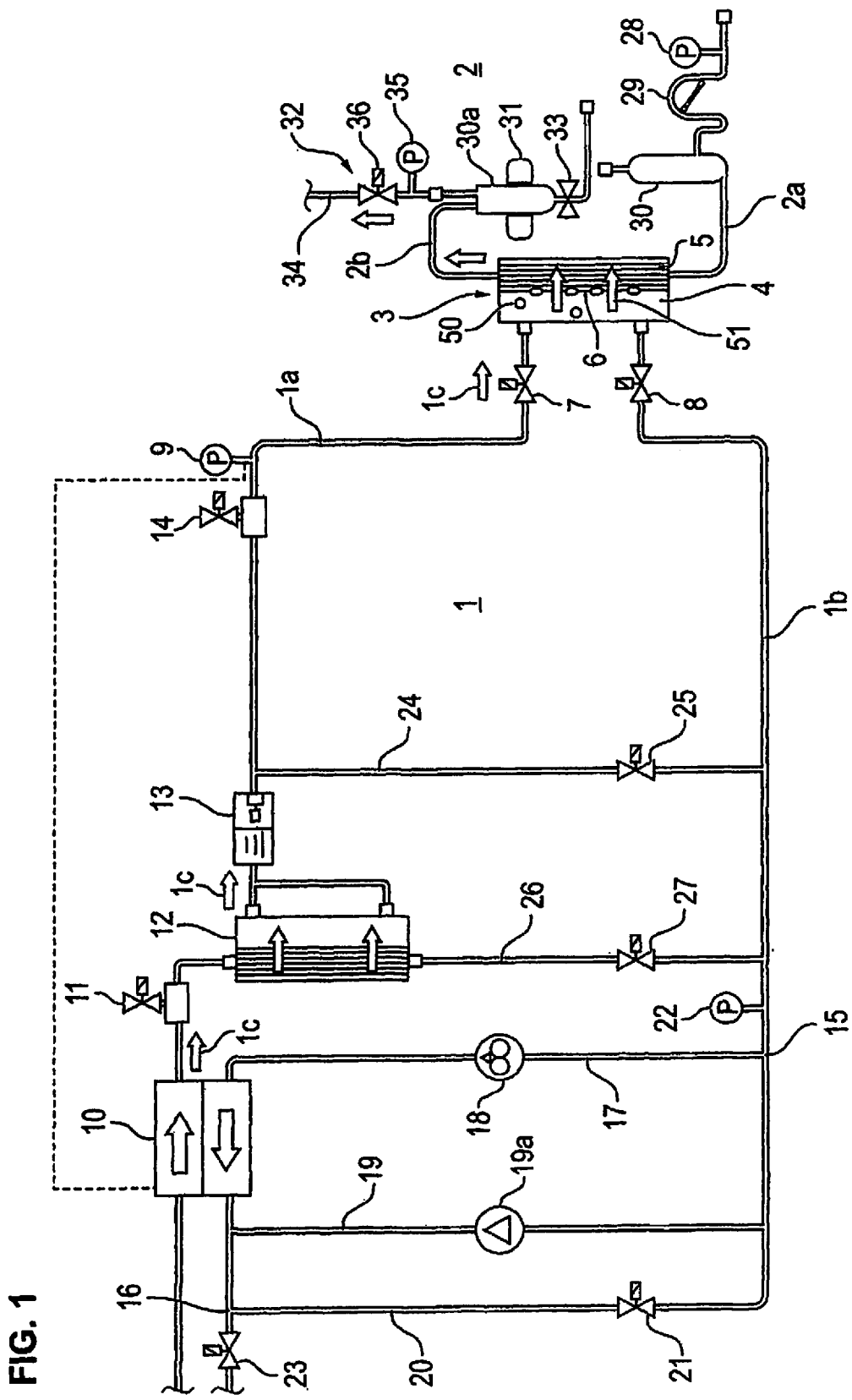
FIG. 1: a schematic representation of the fluid-conducting system of a dialysis machine.

FIG. 1 shows a schematic representation of the fluid-conducting system of a dialysis machine.

The fluid-conducting system comprises a dialyzate circuit 1, a blood circuit 2 and a dialyzer 3. The dialyzer comprises a dialyzate chamber 4, a blood chamber 5 and a semipermeable membrane 6 which separates the dialyzate chamber 4 and the blood chamber 5 from one another. In the capillary dialyzers which are typically used, the blood chamber 5 is formed by the totality of the inner volumes of the hollow fibers and the dialyzate chamber 4 is formed by the inner space of the dialyzer housing surrounding the hollow fibers.

The flow direction of the priming fluid or dialysis fluid in the dialyzate circuit is symbolized by the arrows $1c$ in the Figure.

A feed valve 7 is located in the feed line $1a$ of the dialyzate circuit 1 and a return valve 8 is located in the return line $1b$. The two valves are arranged in the direct vicinity of the dialyzer 4 in the embodiment shown and each represent the closest actuator. A feed pressure sensor 9 is arranged in the feed line $1a$ of the dialyzer 3 and serves the determination of the fluid pressure at the feed side and—in the case of a closed return valve 8—of the fluid pressure in the dialyzate chamber 4 of the dialyzer 3.

The feed line $1a$ furthermore comprises—in the named order in the flow direction—the feed side of a balance chamber 10, a venting valve 11, a sterile filter 12, a conductivity and temperature measurement arrangement 13 and a maintenance valve 14 for any carrying out of a pressure maintenance test. The feed pressure sensor 9 is arranged between the maintenance valve 14 and the feed valve 7.

The return line $1b$ is divided into three between a first branch point 15 and a second branch point 16, wherein a first branch 17 comprises—in the named order in the flow direction—a return pump 18 and the return side of the balance chamber 10. A second branch 19 comprises an ultrafiltration pump 19a and does not pass through the balance chamber 10. A third branch 20 comprises a simple auxiliary valve 21. A return pressure sensor 22 is arranged in front of the branch point 15. A blocking valve 23 is arranged after the second branch point 16.

A bypass line 24 comprising a bypass vale 25 is furthermore arranged between the feed line 1a and the return line 1b. The bypass line 24 branches off from the feed line 1a between the measurement arrangement 13 and the maintenance valve 14 and opens into the return line 1b between the return valve 8 and the return pressure sensor 22.

A retentate line 26 having a retentate valve 27 is furthermore provided and connects the retentate side of the sterile filter 12 to the return line 1b. The retentate line opens into the return line 1b between the bypass line 24 and the return pressure sensor 22.

A supply pump which is not shown in any more detail in the Figure and which is arranged in the feed line 1a at the feed side of the balance chamber 10 serves to convey the priming fluid or dialyzing fluid into the feed line 1a and the dialyzer and to build up pressure—within the framework of the method in accordance with the invention—in the dialyzate chamber.

The blood circuit 2 comprises an arterial line 2a and a venous line 2b, with the dialyzer 3 being connected in the counter-flow principle. The arterial line 2a comprises—in the named order in the flow direction—an arterial pressure sensor 28, a blood pump 29 and, optionally, an arterial bubble trap 30. The venous line 2b comprises—in the named order—a venous bubble trap 30a plus a bubble detector 31 and a venting apparatus 32 as well as a venous clamp 33. The venting apparatus 32 comprises a venting line 34, a venting pressure sensor 35 and a venting valve 36.

The dialyzate chamber 4 of the dialyzer 3 is filled within the framework of a known process before carrying out the method in accordance with the invention for removing air inclusions. In the embodiment shown, the filling takes place within the framework of an online process, with the dialyzer 3 being connected to the dialyzate circuit 1 of the dialysis machine. Alternatively, the filling can also take place using a saline bag.

The method starts after the filling of the dialyzate chamber 4 and before the filling of the blood chamber 5. The blood circuit 2, including the blood chamber 5, is still filled with air on the carrying out of the method.

The feed valve 7 is first held open and the return valve 8 is closed within the framework of the method. A pressure-controlled filling program is started which conveys additional priming fluid into the dialyzate chamber 4 through the feed line 1a using the supply pump. Since the return valve 8 is closed, an overpressure builds up in the dialyzate chamber 4 with respect to the blood chamber 5—in which environmental pressure prevails.

The overpressure arising in relation to the environmental pressure is detected using the feed pressure sensor 9. Once a defined overpressure of, for example, 150 mmHg has been reached, the fluid infeed is stopped and the pressure development or pressure loss measured at the feed pressure sensor 9 is observed during a venting time period. If air flows out of the dialyzate chamber 4 through the membrane 6 into the blood chamber 5, the overpressure in the dialyzate chamber 4 reduces fast again since the dry membrane 6 represents a relatively small flow resistance for air.

The air bubbles are drawn with the reference numeral 50 in FIG. 1 and the flow direction from the dialyzate chamber 4 into the blood chamber 5 is indicated by an arrow 51.

So that no counter-pressure to the atmosphere builds up in the blood chamber 5, the blood chamber 5 is vented toward the atmosphere, for example by means of the ends of the arterial line 2a and/or the venous line 2b or by means of the venting line 34 with an open venting valve 36.

If the overpressure drops fast in the dialyzate chamber 4, it is built up again. If the overpressure in the dialyzate chamber 4 does not drop or only drops very slowly, this means that there is no longer any residual air in the dialyzate chamber 4 or the initially present residual air has already been largely pressed into the still empty blood chamber 5.

Figure 2:
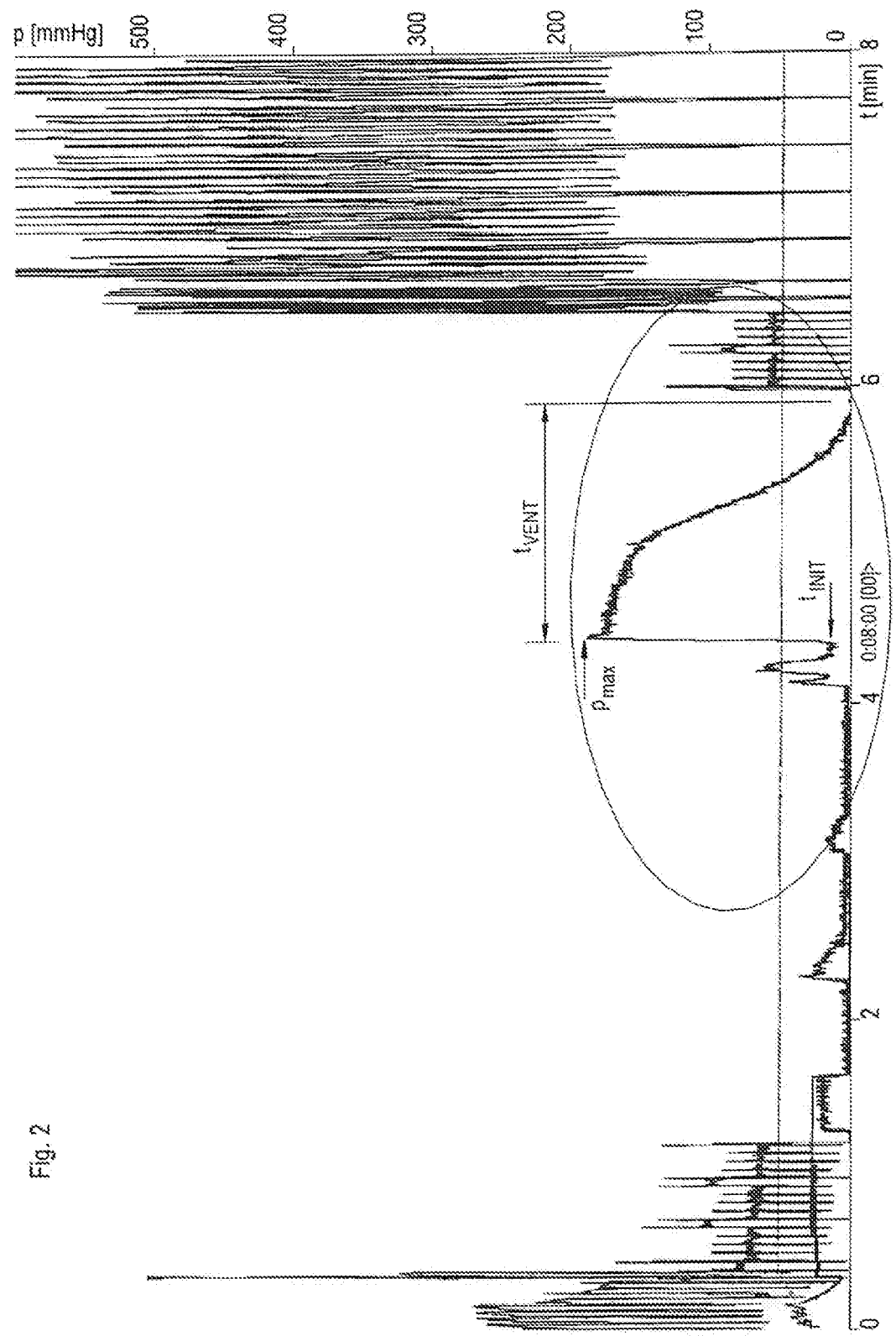
FIG. 2: the time development of the fluid pressure in the dialyzate chamber during the carrying out of a method in accordance with the invention.

A time development of the liquid pressure in the dialyzate chamber 4 determined experimentally within the framework of an experiment is shown in FIG. 2. The fluid pressure in the dialyzate chamber 4 measured at the feed pressure sensor 9 is entered in mmHg on the ordinate in the diagram and the time in minutes is entered on the abscissa. At the time $T_{INIT}$, the return valve 8 was closed and the supply pump was operated further until an overpressure $p_{MAX}$ of 185 mmHg was built up in the dialyzate chamber. This over pressure was completely depleted again relatively fast within a venting time period $t_{VENT}$ of approximately 2 to 3 minutes due to the passage of residual air from the dialyzate chamber 4 into the blood chamber 5.

This behavior is also facilitated by hydrophobic properties of the membrane. As long as the blood chamber 5 of the dialyzer 3 has not yet been filled and is therefore dry, the membrane has a large flow resistance for the aqueous priming fluid.

In addition to a venting, the method in accordance with the invention can also be used by additional parameterization to determine the integrity of the dialyzer membrane 6 or of the interfaces of the dialyzer 3 with the feed line 1a and the return line 1b. A stability criterion is defined here which is, for example, the maximum fluid supply which is required for building up a specific pressure. If this stability criterion of the volume restriction is not observed, conclusions can be drawn from this on a possible rupture of the membrane 6 or on a leaking interface.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method for venting a dialyzer which has a dialyzate chamber at a dialyzate chamber side, a blood chamber and a semipermeable dialyzer membrane separating these two chambers, the method comprising generating an overpressure in the dialyzate chamber with respect to the blood chamber for removing air inclusions lying at a surface of the membrane at the dialyzate chamber side after a filling of the dialyzate chamber and before a filling of the blood chamber, said blood chamber being vented toward the environment during the generating of the overpressure.

2. The method in accordance with claim 1, wherein the overpressure lies in the range up to 2 bar.

3. The method in accordance with claim 1, wherein a pressure build-up is stopped after reaching a predefined overpressure value ($p_{MAX}$) in the dialyzate chamber.

4. The method in accordance with claim 1, wherein the overpressure lies in the range between 50 and 500 mmHg.

5. The method in accordance with claim 1, wherein the overpressure lies in the range between 140 and 220 mmHg.

6. The method in accordance with claim 1, wherein the overpressure lies in the range between 175 and 195 mmHg.

7. The method in accordance with claim 1, wherein the dialyzate chamber is integrated into a dialyzate circuit of a dialysis machine.

8. The method in accordance with claim 1, wherein at least one of a feed side and a return side of the dialyzate chamber is connected to a fluid-conducting system while carrying out of the method.

9. The method in accordance with claim 8, wherein the overpressure is generated by closing a valve arranged at the return side of the dialyzate chamber and simultaneous conveying of further fluid from a feed line of the fluid-conducting system into the dialyzate chamber.

10. The method in accordance with claim 8, wherein pressure building is stopped by stopping a supply pump that provides fluid to the dialyzate chamber.

11. A method for venting a dialyzer which has a dialyzate chamber at a dialyzate chamber side, a blood chamber and a semipermeable dialyzer membrane separating these two chambers, the method comprising generating an overpressure in the dialyzate chamber with respect to the blood chamber for removing air inclusions lying at a surface of the membrane at the dialyzate chamber side after a filling of the dialyzate chamber and before a filling of the blood chamber, and maintaining the overpressure in the dialyzate chamber over a venting time period ($t_{VENT}$) during which the blood chamber is vented.

12. The method in accordance with claim 11, wherein at least one of pressure prevailing in the dialyzate chamber, development of pressure when generating the overpressure, and pressure in the venting time period ($t_{VENT}$) is measured.

13. The method in accordance with claim 12, wherein a characteristic of the measured pressure development in the venting time period ($t_{VENT}$) is used to selectively initiate a repeat of the method or a continuation of a priming procedure.

14. The method in accordance with claim 13, wherein the characteristic of the measured pressure development in the venting time period ($t_{VENT}$) is used to selectively initiate the continuation of a priming procedure selected from the group consisting of a flushing procedure of the dialyzate chamber and a filling of the blood chamber.

15. The method in accordance with claim 12, wherein a characteristic related to the measured pressure development when building up to the overpressure is compared with a corresponding stability criterion which is representative for at least one of an integrity of the dialyzer membrane and an integrity of interfaces of the dialyzate chamber with the fluid-conducting system.

16. The method in accordance with claim 15, further comprising emitting a warning signal on a deviation of the characteristic from the stability criterion.

17. A dialysis machine comprising a dialyzate circuit and a dialyzer which has a dialyzate chamber integrated into the dialyzate circuit, a blood chamber and a semipermeable dialyzer membrane separating these two chambers, and further comprising a control unit on which an algorithm is stored, said algorithm adapted to carry out a method of venting the dialyzer that includes generating an overpressure in the dialyzate chamber with respect to the blood chamber for removing air inclusions lying at a surface of the membrane at the dialyzate chamber side after a filling of the dialyzate chamber and before a filling of the blood chamber, said blood chamber being vented toward the environment during the generating of the overpressure.

18. The method in accordance with claim 11, wherein the step of maintaining the overpressure includes keeping a valve arranged at a return side of the dialyzate chamber closed.

* * * * *